United States Patent [19]

Shinn

[11] Patent Number: 5,339,151
[45] Date of Patent: Aug. 16, 1994

[54] SPECTROMETER FOR LENSOMETER

[75] Inventor: Alan L. Shinn, Berkeley, Calif.

[73] Assignee: Humphrey Instruments Incorporated, San Leandro, Calif.

[21] Appl. No.: 920,746

[22] Filed: Jul. 28, 1992

[51] Int. Cl.$^5$ ............................................... G01J 3/28
[52] U.S. Cl. ....................................... 356/328; 356/124
[58] Field of Search ................. 356/124, 326, 328, 419

[56] References Cited

U.S. PATENT DOCUMENTS

| | | | |
|---|---|---|---|
| 4,293,225 | 10/1981 | Wheaton et al. | 356/417 |
| 4,549,081 | 10/1985 | Ace | 356/124 X |
| 4,652,761 | 3/1987 | Kerr et al. | 356/328 X |

*Primary Examiner*—Jill A. Johnston
*Attorney, Agent, or Firm*—Townsend and Townsend Khourie and Crew

[57] ABSTRACT

A spectrometer is incorporated to a conventional lensometer. The spectrometer includes a uniform extended light source including a light source having visible and ultraviolet emission and an extending integrating sphere including ultraviolet transmission. In the preferred embodiment, an Ebert spectrometer is utilized, although other spectrometers may be used as well. Light is emitted from the light source through the spectacle lens to be tested to a spherical reflecting surface. Upon reflection, the light is incident to a grating, retro reflected to the spherical surface and thereafter reflected for incidence to a charge coupled device for analysis of the generated spectrum. The system is provided with a slit and a field stop dimensioned so that through all ranges of lenses expected to be tested within designated tolerances of sphere, cylinder and prism, the spectrometer sees only and always a portion of the uniform extended light source. Preferably, the stop is located exterior of the spectrometer—although location of the stop at the reflecting surface, or grating can be operable. There results a lensometer capable of measurements of lens power and glass absorption characteristics, the latter measurement not being affected by the power or decentration of the measured lens.

15 Claims, 3 Drawing Sheets

SPECTROMETER FOR LENSOMETER

This invention relates to lensmeters for measuring the power of spectacle lenses and more particularly to a lensometer incorporating a spectrometer for providing a simultaneous spectral reading with lens prescription. The incorporated spectrometer includes a measurement of light absorption which is independent of lens power whereby the measurement of the spectral absorption qualities of the material of the measured spectacle lens is independent of the power of the measured lens.

BACKGROUND OF THE INVENTION

Spectacle lenses are being manufactured from an increasingly wide number of materials having varied spectral characteristics. It has become important not only to know the power of such lenses but to be aware of the lenses spectral absorption characteristics. The reasons for knowing the spectral characteristics of such lenses can be easily summarized.

First, and most importantly, the ophthalmic community has become increasingly aware of the importance of the ultraviolet absorption characteristics of spectacle lenses and sunglasses. Simply stated, ultraviolet radiation in unacceptably large exposure can be harmful to the eye. Unfortunately, with modern glasses utilized in spectacle lenses, such absorption characteristics vary widely. Glasses are known which diminish light in the visible spectrum while having reduced or little effect on light in the ultraviolet. This characteristic of lenses causes the pupil of the eye to dilate to the maximum aperture to accommodate light in the visible spectrum—letting in what can be harmful amounts of ultraviolet radiation.

Secondly, spectral readings on the absorption characteristics of spectacle lenses can be a convenient way to measure the color of the lenses for either order or comparison. Unfortunately, eye glasses now come in so many different shades or colors that meaningful comparison or specification of the material in terms of their measurable spectral characteristics is not possible. Consequently, there is no way to "compare" quantitatively the color of eye glasses. More over, there is no acceptable way to specify eye glasses by their color.

Thirdly, when the material of such eye glasses is measured for its spectral characteristics, the eye glass is already configured into a lens. This being the case, in all known spectrometers, the power of the lens effects the spectral measurement of the glass of the eye glasses. Since prescriptions vary widely, the impact of the prescription upon the measurement of the spectral characteristics of the glass is not predictable—especially when both the power of the lens and the absorption characteristics of the lens both constitute unknowns at the beginning of measurement.

SUMMARY OF THE INVENTION

A spectrometer is incorporated to a conventional lensometer. The spectrometer includes an extended light source including a light source having visible and ultraviolet emission and an extending diffuser including ultraviolet transmission. In the preferred embodiment, an Ebert spectrometer is utilized, although other spectrometers may be used as well. Light is emitted from a light source through the spectacle lens to be tested to a spherical reflecting surface. Upon reflection, the light is incident to a grating, retro reflected to the spherical surface and thereafter reflected for incidence to a detector array for analysis of the generated spectrum. The system is provided with a slit and a field stop dimensioned so that through all ranges of lenses expected to be tested within designated tolerances of sphere, cylinder and prism, the spectrometer sees only and always a portion of the extended light source. Preferably, the stop is located exterior of the spectrometer—although location of the stop at the reflecting surface, or grating can be operable. There results a lensometer capable of measurements of lens power and material absorption characteristics, the latter measurement not being affected by the power of the measured lens.

OTHER OBJECTS, FEATURES, AND ADVANTAGES

An object of this invention is to disclose a spectrometer for lenses that can measure spectral characteristics of the material of the lens independent of the power of the lens placed within the spectrometer. According to this aspect, a spectrometer is provided with a uniform extended light source. Light from the uniform extended spectrometer light source is routed through a slit and field stop combination dimensioned so that at all anticipated powers of lenses—in sphere, cylinder and prism—the spectrometer only and always sees a portion of the extended light source. There results a spectrometer capable of measuring the absorption characteristics of material configured into a lens where the power of the lens is does not impact the measured spectral characteristics of the lens.

A further object of this invention is to disclose the incorporation of such a spectrometer to a lensometer. According to this aspect of the invention, a spectrometer according to this invention is drawer mounted to a conventional lensometer. When measurement of the spectral absorption characteristics is required, the lens under test is removed from the lensometer, placed to the drawer mounted spectrometer, and the measurement is taken. An instrument is produced which enables measurement of two lens unknowns including the sphere, cylinder and prism of the lens as well as the spectral absorption characteristics of the material of a lens.

An additional object of this invention is to disclose a preferred optical train for a such spectrometer. Specifically, an Ebert type lens train is utilized. Light from the uniform extended light source passes through a slit and field stop. The slit and field stop are dimensioned to permit the detector to view only a portion of the light source even though an anticipated range of lenses having varying sphere, cylinder and prism may be measured within the spectrometer. The stop is preferably exterior of the spectrometer; alternately it can be within the spectrometer either at the grating, or mirror. The slit is extended relative to the detector and positioned in a plane so as to provide on the central portion of the detector with a sharply focused image which is not effected by the astigmatic aberrations of the off center reflection of the spherical reflecting surface of the Ebert spectrometer. A slot for vignetting the slit is provided to cut off portions of the light passing through the slit which can not reach the detector but could degrade the signal due to internal scattering. The slot is placed in a plane so that its effective edges are sharply focused onto the detector surface. The disclosed detector is a photodetector line array for accurate image of the received spectrum. A simple spectrometer having relative high performance characteristics results.

A further object of this invention is to disclose a spectrometer actuated by a flash lamp having consistent spectral characteristics. According to this aspect, the spectrometer is calibrated to an intensity monitoring photo cell by having the system referenced by flashing the light source without the presence of a lens to be tested. Thereafter, and when the lens is inserted to the spectrometer—further flashes of the light source are further monitored by the intensity monitoring photo cell. Adjustment of the received spectral measurement of the lens can occur—even though such brilliance in the flashing source varies.

BRIEF DESCRIPTION OF THE DRAWINGS

Other objects, features and advantages of this invention will be more apparent after referring to the following specification and attached drawings in which.

DESCRIPTION OF THE PREFERRED EMBODIMENT

Figure 1:
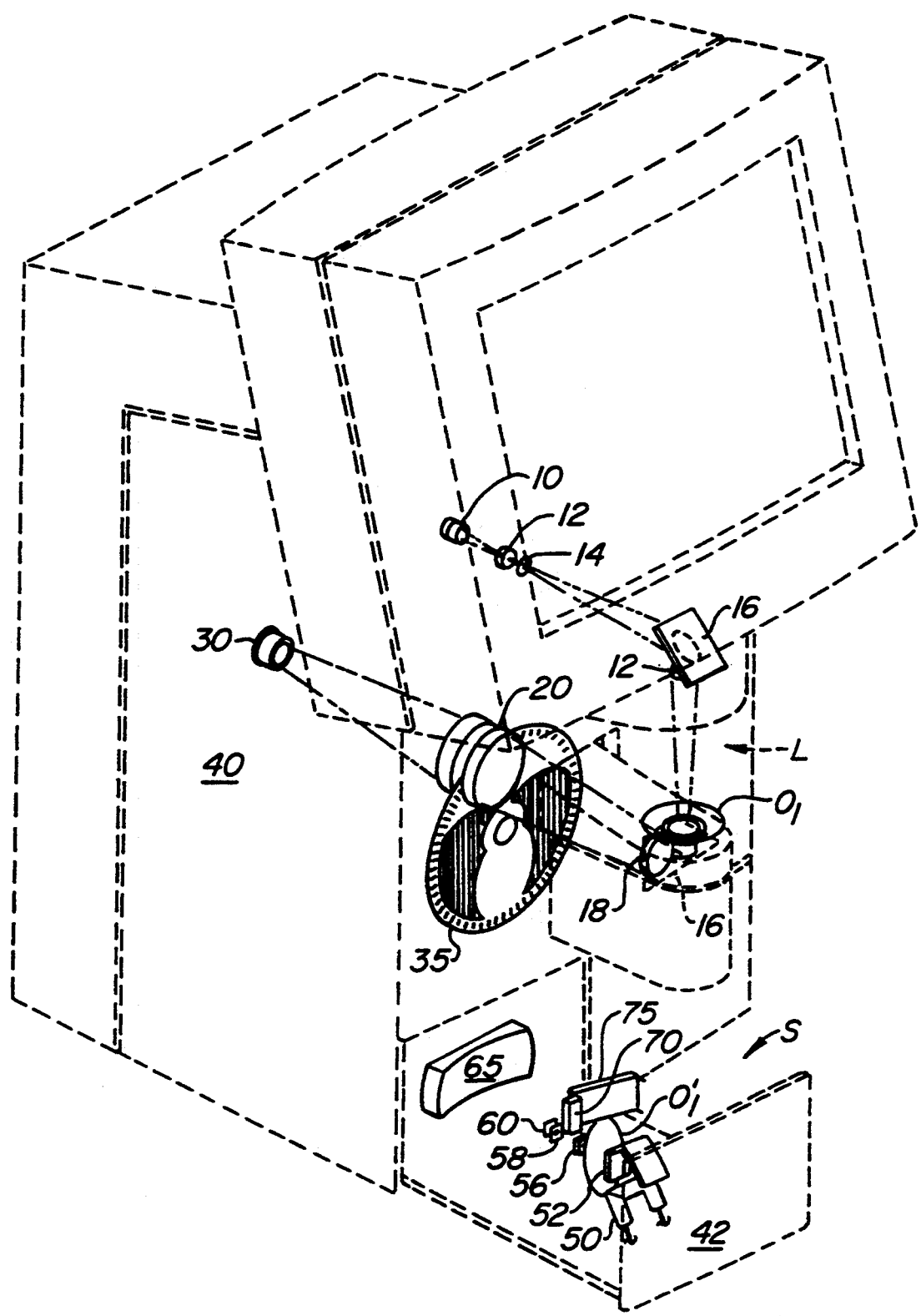
FIG. 1 is a perspective view of a lensometer having the spectrometer of this invention incorporated to the lower body of the lensometer.

Referring to FIG. 1, a prior art lensometer L is illustrated, including a light source 30, optics 4, 12, 18 and 20, and aperture 14 and mirrors 16. Light from light source 30 is pupilled through a suspect optics $O_1$, which optic $O_1$ thereafter passes the light through Optics 12 to detector 10. A moving boundary locus 35 occults light sources from light source 30, in accordance with the sphere, cylinder and axis of the Optic $O_1$.

The spectrometer of this invention is drawer-mounted to the bottom of the lensometer case 40, at drawer 42. The spectrometer includes a lamp 50 and integrating sphere 52. Optic $O_1'$ is moved to a measurement position interior the spectrometer S. A field stop 56 spectrometer slit 60 as well as a slit limiting stop 58 prepare light received from the diffuser for passing to a mirror 65, a grating 70, with retroreflection to mirror 65 and final impingement on a Charge Couple Device (CCD) detector 75. Having set forth the component portions, attention can now be devoted to the operating parameters of the disclosed invention.

Light source 50 emits in both visible and ultraviolet ranges. Other wavelengths may be included in the spectrum of light source 50.

Figure 2:
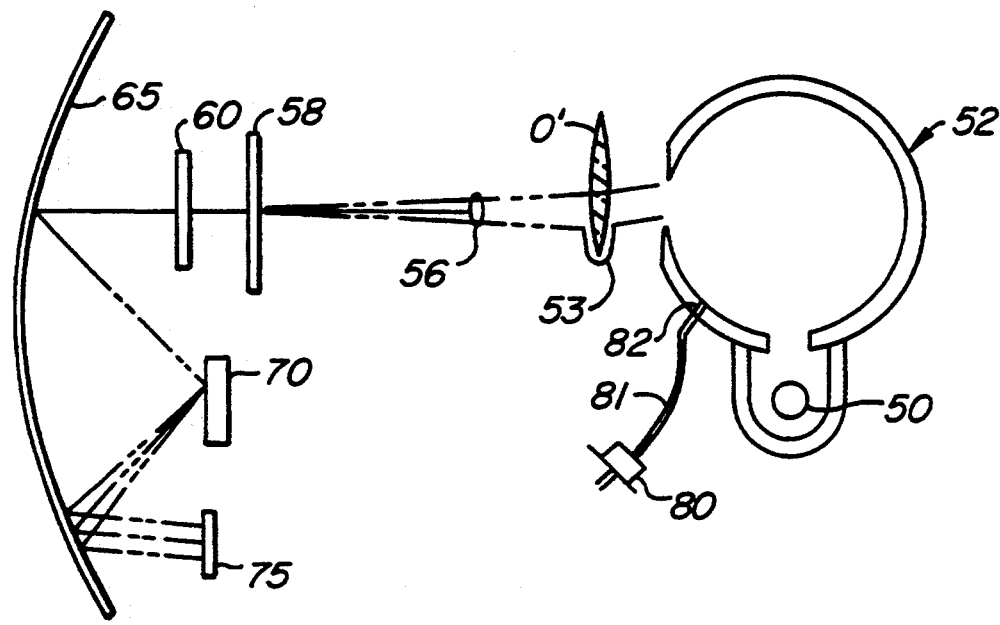
FIG. 2 is a side elevation view of the spectrometer only with the illustrated slit being shown in side elevation within the plane of the figure and the rulings on the grating being shown normal to the plane of the paper.
Figure 3:
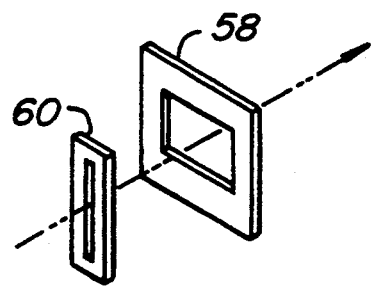
FIG. 3 is a perspective view of the slit used for producing the spectral separation with a slot surrounding the upper and lower portions of the slit for vignetting those portions of the image of the slit at the detector in which the slot limits the quantity of light entering the instrument to only useful rays thereby reducing "scattered" light; and, FIG. 4 is a perspective view schematic of a spectrometer similar to FIG. 2 showing the spectrometer without the slit configuration and illustrating an alternate type of spectrometer utilizing the invention herein for the measurement of lens transmission characteristics.

Referring to FIG. 2, it is preferred if light source emits its light into integrating sphere 52 which in turn causes the light to exit its aperture uniformly in both the visible and ultraviolet spectrum.

The lens under test $O_1'$, is mounted to a lens holder 53. Field stop 56, in combination with slit 60, defines a view of less than all of the light source.

In FIG. 2, it will be noticed that I have placed the field stop external to the spectrometer. This prevents light scattered from the field stop from being detected at CCD Detector 75.

Further, field stop 56, in combination with slit 60, limits the external field of view of the spectrometer to be much smaller than the angle subtended through the optics $O_1'$ by the extended source. When this is done, the instrument field of view will always be within the extended source. As a consequence, the measurement of spectral absorption will be independent of the power of the lens.

Preferably, slit 60 is positioned with respect to mirror 65 so that its longer edges are imaged sharply focused on detector 75, these imaged edges being oriented at right angles to the long dimension of the linear CCD 75. As those versed in the art will recognize, due to the astigmatism imaging effect of the off axis use of spherical mirror 65, it is not possible to image the longer edges and shorter edges of slit 60 sharply on the CCD surface at the same time. Therefore, I have placed slot 58 in a plane different from that of slit 60 such that its edges at right angles to the longer edges of slit 60 are sharply focused by mirror 65 on detector 75. Slot 58 thereby sharply limits either end of slit 60, preventing light that is not useful from entering the spectrometer, scattering off various surfaces and degrading the signal as it reaches detector 75. Slot 58 is made wide enough so that it is not the limiting stop in the narrow dimension of slit 60. As stated above, this dimension is controlled by field stop 56.

Slot 58 limits either end of the slit 60, preferably the slot 58 is positioned so that it will focus its edges on the CCD detector. As a spherical mirror 65 is used for focus in the disclosed Ebert-type spectrometer, astigmatic de-focus from the ends of the slit is attenuated by the action of the disclosed slot 58. Light source 50 is preferably a gas discharge lamp. In the operation of the system here disclosed, it is typically flashed before optic $O_1'$ is inserted. The response of the system is stored. Thereafter, the system is again strobed with the lens under test $O_1'$ being in place. By comparison with the original flash, the absolute external transmittance of the optic $O_1'$ is calculated It will be understood that some flash lamps 50 vary in intensity from flash to flash. Consequently, I use a detector 80 to monitor the flash of the lamp. Detector 80 is connected via fiber optic 81 through integrating sphere 52 at aperture 82. The output of detector 80 is used to compare the intensity of the lamp at the time of calibration (when no optic was in the optical train) compared to the intensity at the time of measurement. The ratio of the two measurements is thereafter used to correct transmittance values of the lens.

The reader will understand that the disclosed Ebert-type spectrometer is exemplary. Other types of spectrometers could be used as well.

The fact that the spectrometer measurement is not affected by changed power of the lens is a phenomenon that has been observed. An explanation can be offered for this observed effect.

Any finite point in the integrating sphere 52 exit aperture emits light in a hemispherical pattern. The question then becomes: how will a particular lens of an arbitrary power transmit light from such a hemispherical pattern?

The lens will transmit light to the detector from the hemispherical emission pattern of each finite point at a solid angle restricted to its particular focus. Thus, both the total area (that is, the total number of finite points emitting a hemispherical pattern) of the integrating sphere emitting light through the lens, as well as the solid angle of light received from each finite point, will vary—as the focus of the lens placed within the spectrometer varies. It turns out that as long as the essential constant illumination of the integrating sphere is the only target of the view, the total luminance of the light passing through the lens will remain unchanged.

Where the area of the integrating sphere exit aperture viewed by the detector increases with the insertion of a lens, the solid angle of the light from each finite point decreases. Conversely, where the area of the integrating sphere exit aperture viewed by the detector decreases with the insertion of a lens the solid angle of light from each finite point increases. Total light transmitted remains the same so long as only a part of the integrating sphere is the view target of the detector.

Figure 4:
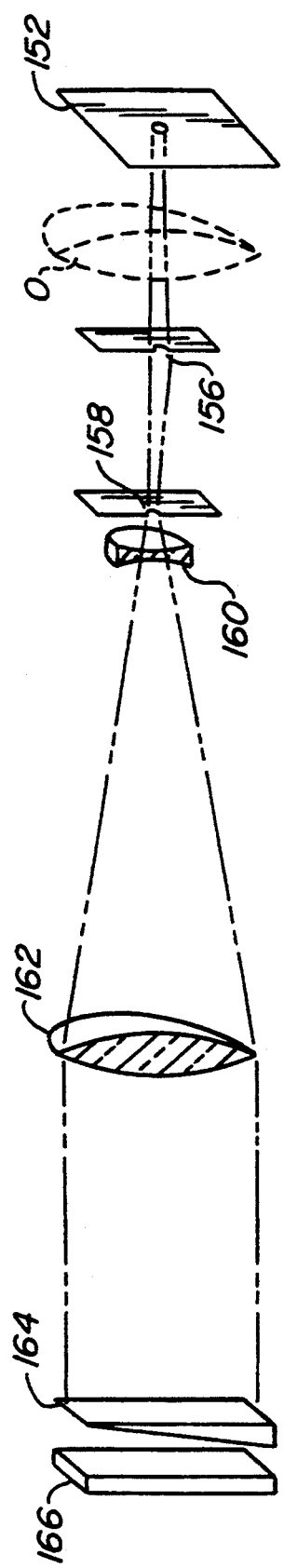

Referring to FIG. 4, the spectrometer portion of a lensometer similar to that shown in FIG. 1 is set forth. Extended light source 152 is illustrated with suspect optic O. Paired pin holes 156, 158 project a finite bundle of light from extended source 152 through optic O. After passage through the second pinhole 158 (where a collimated beam is projected), respective concave lens 160 and convex lens 162 combine to provide an expanded collimated beam. This beam thereafter passes through a wedge dichroic filter 164 with the spectral transmission being read at linear CCD 166.

Again, it will be observed that the power of the lens utilized will make no difference in the observation of the spectrometer. Deflection of the lens because of its power will resort in deflection to the extended light source—but never a change in spectral transmission characteristic.

What is claimed is:

1. In a spectrometer for measuring the spectral transmission of the material of a lens to be tested independent of the power of such lens to be tested comprising:
   a mounting for holding said lens to be tested during measurement by said spectrometer;
   a uniform extended light source for passing light through said lens to be tested in said mounting, said extended light source having a dimension selected with respect to said lens to be tested, for enabling light passing through said lens to be tested to be incident on at least a portion of said light source at all anticipated powers and amounts of decentration of said lens to be tested;
   a light path between said uniform extended light source and a detector, said light path passing through said lens to be tested therebetween;
   means for producing from said lens to be tested a constant size bundle of rays in said light path, said means including first and second stops between said lens to be tested and said detector;
   spectrometer means for receiving said light from said constant size bundle of rays for the analysis of a spectral image of light passing through said lens to be tested; and,
   said detector coupled to said spectrometer means for receiving said spectral image of light from said uniform extended light source passing through said lens to be tested in said holder.

2. The invention of claim 1 and wherein said spectrometer means includes:
   a lit between said lens to be tested and said detector;
   a grating placed between said slit and said detector for producing from light passing through said slit a spectral image at said detector of said light from said uniform extended light source and said lens to be tested to and through said slit to said detector; and,
   a field stop in combination with said slit for producing a partial image of said light source for all ranges of sphere, cylinder and prism of lenses to be tested in said spectrometer whereby said spectral measurement of said lens to be tested is independent of the power and decentration of said lens to be tested.

3. In a spectrometer for measuring the spectral transmission of the material of a spectacle lens to be tested independent of the power of such lens to be tested comprising:
   a mounting for holding said lens to be tested during measurement by said spectrometer;
   a uniform extended light source for passing light through said lens to be tested in said mounting, said extended light source having a dimension selected with respect to said lens to be tested, for enabling light passing through said lens to be tested to be incident on at least a portion of said light source at all anticipated powers and amounts of decentration of said lens to be tested;
   a detector for receiving a spectral image of light from a uniform extended light source passing through said lens to be tested in said mounting;
   a light path between said uniform extended light source and said detector for passing the light from said source passing through said lens to be tested to said detector for analysis by said detector;
   a slit between said lens to be tested and said detector;
   a grating placed between said slit and said detector for producing from light passing through said slit a spectral image at said detector of said light from said uniform extended light source and said lens to be tested to and through said slit to said detector; and,
   a field stop in combination with said slit for producing a partial image of said light source for all ranges of sphere, cylinder and prism of lenses to be tested in said spectrometer whereby said spectral measurement of the transmission of said lens to be tested is independent of the power and decentration of said lens to be tested.

4. The invention of claim 3 and wherein:
   said field stop is between said slit and said lens to be tested.

5. The invention of claim 3 and wherein:
   said field stop is at a mirror.

6. The invention of claim 3 and wherein:
   said field stop is at said grating.

7. The invention of claim 3 and wherein:
   a slot is placed adjacent said slit, said slot having a dimension to delimit said slit at the top and bottom thereof for truncating the top and bottom of the image produced by said slit; and,
   means in said light path for imaging said slot to said detector for delimiting the image of said slit at said detector.

8. The invention of claim 3 and wherein:

said light path includes a spherical mirror between said grating and said slit.

9. The invention of claim 3 and wherein said light source comprises a flash lamp.

10. The invention of claim 9 and including:
a photo cell monitoring said uniform extended light source, said photo cell having an output; and,
means for moderating computed transmission values of said lens to be tested responsive to said output of said photo cell.

11. A process for measuring the spectral transmission of the material of spectacle lens to be tested independent of the power and decentration of said lens to be tested comprising the steps of:
providing a mounting for holding said lens to be tested during measurement;
providing a uniform extended light source for passing light through said lens to be tested in said mounting, said extended light source having a dimension selected with respect to said lens to be tested for enabling light passing through said lens to be tested to be incident on at least a portion of said light source at all anticipated powers and amounts of decentration of said lens to be tested said uniform extended light source is unchanged;
placing a spectacle lens to be tested having said material for spectral analysis on said mounting;
providing a light path between said spectacle lens to be tested and a spectrometer having first and second limiting stops for passing a controlled bundle of rays from the light from said uniform extended light source passing through said lens to be tested;
providing a spectrometer having a detector plane to receive said light from said light path;
providing a photodetector at a detector plane; and,
detecting the spectral image at said detector plane by deflecting said spectral image to said photodetector at said spectral plane to obtain a measurement of the transmission of the material of said spectacle lens to be tested independent of the power and decentration of said spectacle lens to be tested.

12. The process of claim 11 and wherein:
said step of providing a spectrometer includes
providing a slit between said lens to be tested and said photodetector;
providing a grating placed between said slit and said photodetector for producing from light passing through said slit a spectral image at said photodector of said light from said extended light source and said lens to be tested to and through said slit to said detector; and,
providing a field stop in combination with said slit for producing a partial image of said light source for all ranges of sphere, cylinder and prism of lenses to be tested in said spectrometer whereby said spectral measurement of the transmission of said lens to be tested is independent of the power and decentration of said lens to be tested.

13. A process for measuring the spectral transmission of the material of spectacle lens to be tested independent of the power and decentration of said lenses comprising the steps of:
providing a mounting for holding said lens to be tested during measurement;
placing a spectacle lens to be tested for spectral analysis on said mounting;
providing a uniform extended light source for passing light through said lens to be tested in said mounting, said extended light source having a dimension selected with respect to said lens to be tested, for enabling light passing through said lens to be tested to be incident on at least a portion of said light source at all anticipated powers and amounts of decentration of said lens to be tested;
providing a detector plane;
providing a light path between a uniform extended light source and said detector plane for passing the light from said source passing through said lens to be tested to said detector plane for analysis;
providing a slit between said lens to be tested and said detector plane;
providing a grating placed between said slit and said detector plane for producing from light passing through said slit a spectral image at said detector plane of said light from said extended light source and said lens to be tested to and through said slit to said detector plane;
placing a field stop in combination with said slit for producing a partial image of said light source for all ranges of sphere, cylinder and prism of lenses to be tested in said spectrometer;
projecting and detecting the spectral image at said detector plane to obtain a measurement of the transmission of the material of said spectacle lens to be tested, independent of the power and decentration of said spectacle lens to be tested.

14. The process of claim 13 and where said providing a field stop step includes:
providing a field stop between said slit and said lens to be tested.

15. The process of claim 13 and where said providing a uniform extended light source step includes:
flashing said uniform extended light source.

* * * * *